United States Patent [19]
Hauer

[11] 3,991,309
[45] Nov. 9, 1976

[54] METHODS AND APPARATUS FOR THE CONTROL AND ANALYSIS OF X-RAYS

[75] Inventor: Allan Hauer, Rochester, N.Y.

[73] Assignee: University of Rochester, Rochester, N.Y.

[22] Filed: July 9, 1975

[21] Appl. No.: 594,846

[52] U.S. Cl. .............................. 250/272; 250/273; 250/505; 250/514
[51] Int. Cl.² ...................................... G01N 23/20
[58] Field of Search ........... 250/272, 273, 274, 275, 250/277, 505, 514

[56] References Cited
UNITED STATES PATENTS

| | | | |
|---|---|---|---|
| 3,376,415 | 4/1968 | Krogstad | 250/274 |
| 3,381,127 | 4/1968 | Spielberg | 250/272 |
| 3,591,803 | 7/1971 | Spielberg | 250/273 |
| 3,769,507 | 10/1973 | Kenney | 250/272 |

*Primary Examiner*—Craig E. Church
*Attorney, Agent, or Firm*—Martin Lukacher

[57] ABSTRACT

Fast X-ray excitation processes such as occur during nuclear fusion reactions where high energy laser pulses hit a target, as for the purpose of stimulating atomic emission, may be analyzed by interposing a crystal in the path of the X-rays. The X-rays are transmitted through this crystal by means of the anomalous transmission or Bormann effect. A periodic strain field is established in the crystal to enable or inhibit anomalous transmission. The transmitted radiation is received by a measurement system which is operated in synchronism with the strain field. A solid state shuttering mechanism is obtained which rapidly interrupts the X-rays so that they can be measured even when produced by fast X-ray excitation processes. Various methods and apparatus for producing the periodic strain field are described, particularly electrostrictive techniques, piezoelectric techniques using separate transducers mounted on the crystal or the piezoelectric properties of the crystal itself and techniques for stimulating acoustic vibration by means of an optical beam.

41 Claims, 9 Drawing Figures

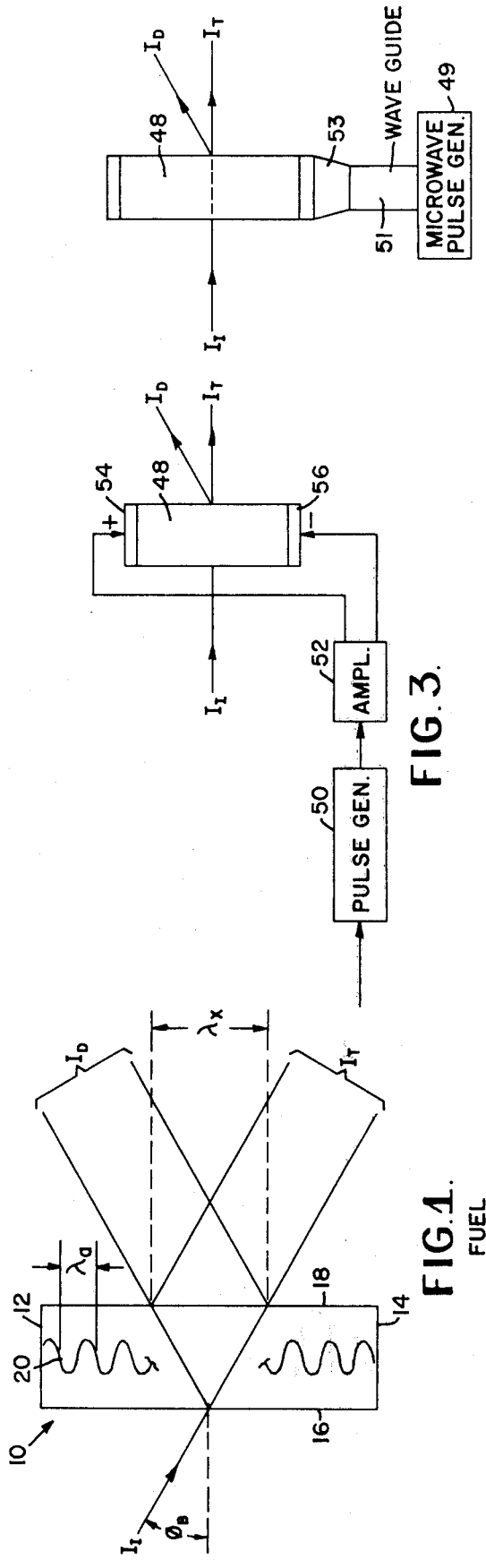
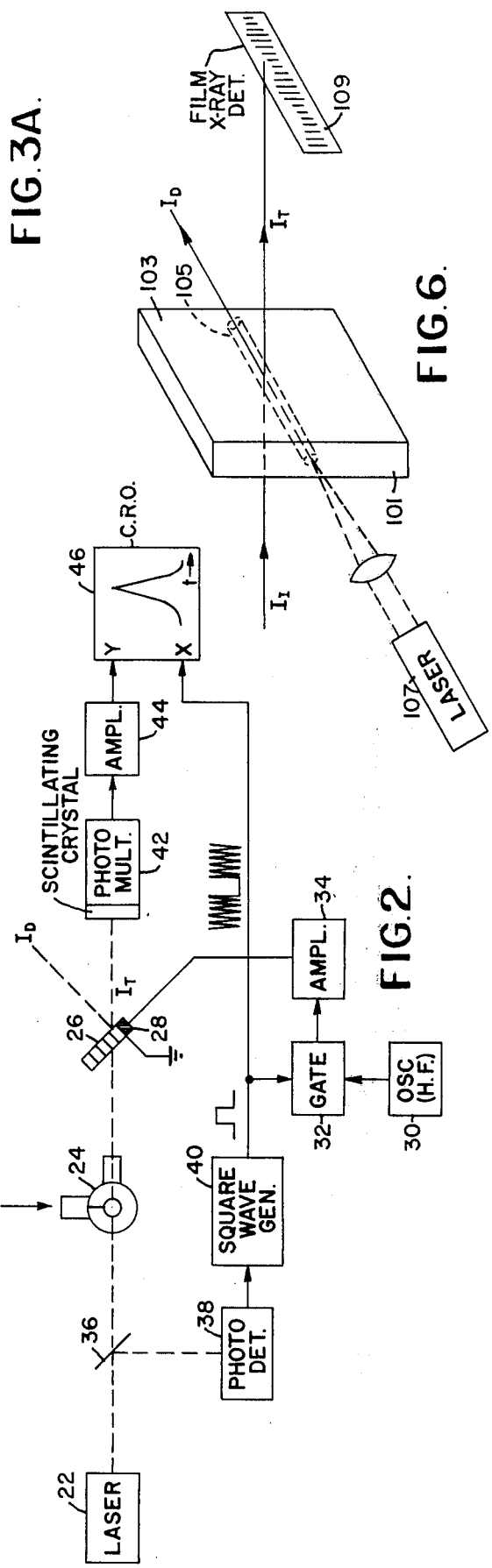

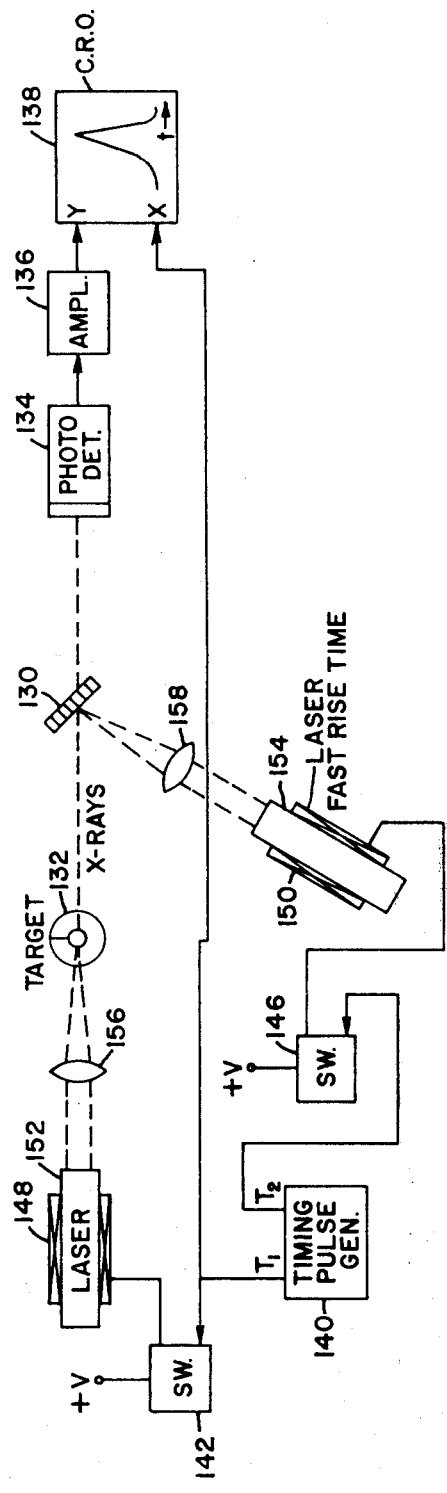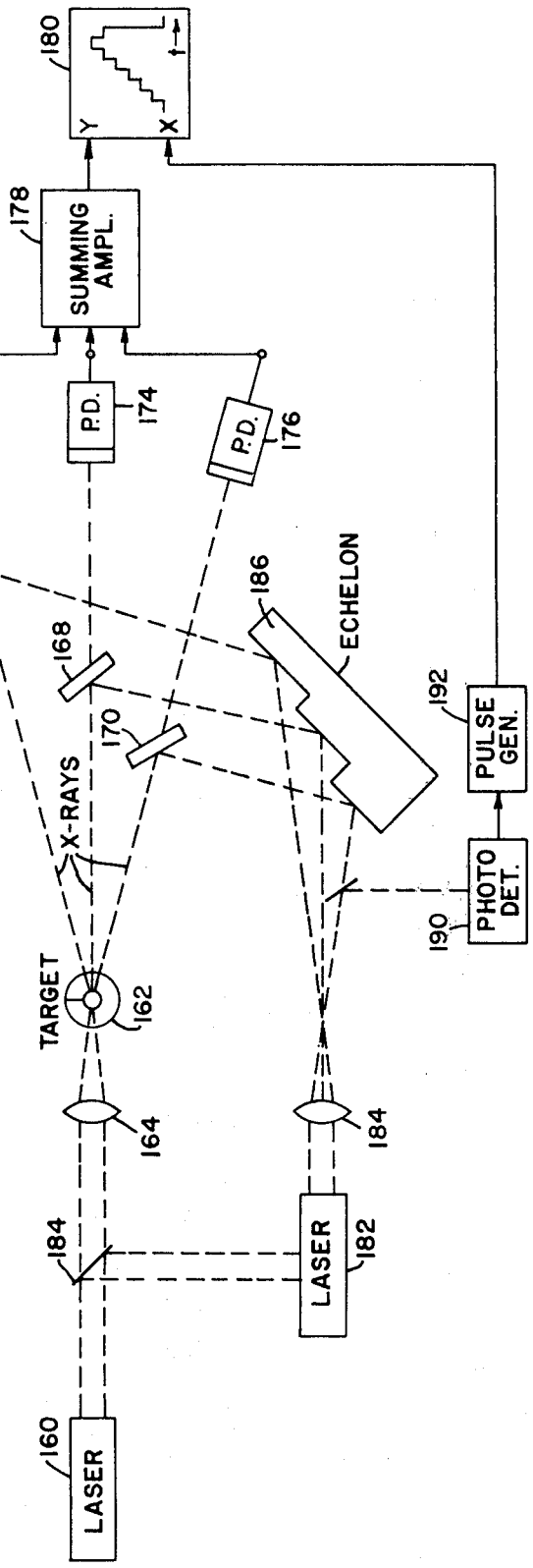
FIG. 7.
FIG. 8.

METHODS AND APPARATUS FOR THE CONTROL AND ANALYSIS OF X-RAYS

The present invention relates to methods and apparatus for the control and analysis of x-ray radiation and particularly to improved methods and apparatus for providing x-ray shutter and modulation mechanisms.

The invention is especially suitable for use in the control and analysis of x-rays produced by very fast x-ray excitation processes. Such processes occur in a laser produced plasma resulting when a high intensity laser pulse strikes a target of material of moderate atomic number (e.g., deuterium or tritium). The invention is also applicable for the control and analysis of X-ray emission from other X-ray sources, and particularly when an understanding of the temporal characteristics of the X-ray radiation is desired.

The analysis of very fast excitation processes has presented a challenge both in the field of plasma physics and optical physics. X-ray emission characteristics may enable laser plasma mechanisms to be better understood. For example, the temporal profile of the intensity of X-ray radiation may be related to the absorption of laser power in the thermonuclear fuel element used in a laser fusion reaction. The X-rays emanating from a laser produced plasma occur in fast bursts and their measurement must take place in correspondingly short periods of time. The devices which have been suggested for the purpose of making measurement of these fast and short lifetime X-ray emissions are principally of the type known as "streak" cameras. These are complex electro-optical devices available only as costly laboratory instruments. Further information respecting streak cameras may be had by reference to an article appearing in the *Review of Science Instruments*, Vol. 43, No. 12, December, 1972, pps. 18–19, by M. Y. Scheleb, M. C. Richardson, and H. A. Alcock, entitled "Operation of a Grid-Shuttered Image Converter Tube in the Picosecond Region". Electromechanical X-ray shutters (see, e.g., U.S. Pat. No. 3,643,095) are too slow to follow fast X-ray excitation processes.

Certain effects on X-ray radiation have been observed in crystal structure. For example, the control of X-ray transmission by diffraction effects has been suggested (see U.S. Pat. No. 2,853,617). Optical energy has been modulated by means of changing the internal structure of a crystal (see U.S. Pat. Nos. 3,365,581; 3,509,489; 3,665,255; and 3,869,197). It has also been observed that anomalous or Bormann transmission of X-rays through a crystal is affected by strains and elevated temperatures within the crystal. Reference may be had to an article by P. P. Ewald, entitled "Crystal Optics for Visible Light and X-rays", appearing in *Reviews of Modern Physics, Vol.* 37, No. 1, January, 1965, p. 46, for a detailed discussion of the Bormann Effect. An article by L. P. Hunter entitled "X-Ray Measurement of Microstrains in Germanium Single Crystals", appearing in the *Journal of Applied Physics*, Vol. 30, No. 6, June, 1959, discusses the effect of strain on Bormann or anomalous transmission in crystals. An article by B. W. Batterman entitled "Effect of Thermal Vibrations on Diffraction From Perfect Crystals, I. The Case of Anomalous Transmission", appearing in the *Physical Review*, Vol. 126, p.1, May, 1962 discusses the effects of temperature on anomalous or Bormann Transmission.

It has been discovered, in accordance with the invention that where the strains are introduced temporarily in a crystal, and particularly where the strains are periodic in nature as in the form of acoustic waves, very fast switching or shuttering of anomalous or Bormann transmission of X-rays can be obtained. The periodic waves may be piezoelectrically excited acoustic waves (say shear or compressional waves) having a displacement in a direction perpendicular to the diffracting lattice planes in the crystal. The periodicity of the strain field which is stimulated in the crystal is preferably less than the extent of spreading of an X-ray as it passes through the crystal. The requisite periodicity may be obtained by exciting extremely high frequency vibrations in the crystal; for example, of the order of 1 MHz to 1 GHz, thus providing a wavelength of the vibration such that the lattice planes of the crystal shift and do not remain at the nodes of a standing wave pattern produced in the crystal by the incident X-rays. The atoms of the lattice planes are then capable of absorbing the X-rays. It should be understood of course, that this invention is not limited to any theory of operation such as the theory set forth above whereby anomalous transmission and the Bormann effect is explained by reason of a critical match between a standing wave electric field and an extended path of perfect periodicity in the crystal, when X-rays incident to the lattice planes of the crystal form the Bragg angle with the lattice planes.

In accordance with the invention the periodic strain field may be established by means of a transducer mounted on the crystal which launches an acoustic wave in the crystal. By acoustic wave, it is meant a vibrating condition in the crystal at any frequency including, but not limited, to frequencies in the audible range. Thus a suitable acoustic wave may be introduced by applying high frequency electric signals, say of the order of 10 MHz, to the transducer. Alternatively, acoustic waves may be launched in the crystal by applying microwave pulse energy to an end face of the crystal or by applying a high voltage pulse across the crystal in a direction perpendicular to the lattice planes; the crystal having piezoelectric properties. It is desirable when extremely fast rise time acoustic waves are needed, to excite such waves by means of a high intensity optical beam which is incident on the crystal in the same region as the X-rays.

The anomalous transmission of X-rays through the crystal may be measured synchronously with the launching of the acoustic wave. Alternatively, the acoustic waves may be launched and measurement of the anomalous transmission made synchronously with the generation of the X-rays as by, or simultaneously with the output of a laser which excites the emission of the X-rays as by means of a laser produced plasma.

A temporal profile of the intensity of the X-ray emission may be obtained by means of a plurality of crystals disposed to receive X-rays which emanate from a target in different ones of a plurality of directions. Acoustic waves are launched in these crystals sequentially so as to interrupt anomalous transmission through different ones of the crystals in sequential order. X-ray detectors responsive to the X-ray transmitted through each crystal provide signals which vary in amplitude in accordance with the variation in intensity of the radiation emanating from the target with time.

It is therefore an object of the present invention to provide improved methods of and apparatus for controlling the transmission of X-ray radiation.

It is another object of the present invention to provide improved methods of and apparatus for shuttering and/or modulating X-ray radiation.

It is a further object of the present invention to provide improved methods of and apparatus for the analysis of X-rays, particularly X-rays produced by fast excitation processes.

It is a still further object of the present invention to provide improved methods of and apparatus for analysis of X-ray radiation from plasmas produced as a result of laser irradiation of targets.

It is a still further object of the present invention to provide improved methods in apparatus for switching X-rays on and off.

It is a still further object of the present invention to provide improved X-ray shutter apparatus.

It is a still further object of the present invention to provide improved methods of and apparatus for controlling Bormann transmission to provide an X-ray shuttering mechanism.

It is a still further object of the present invention to provide an improved method of and apparatus for electromagnetic excitation of crystals in a manner to control X-ray transmission of the anomalous or Bormann type whereby to provide a fast X-ray shuttering mechanism.

The foregoing and other objects and advantages of the present invention will become more apparent from a reading of the following description in connection with the accompanying drawings in which:

FIG. 1 is a schematic diagram illustrating an X-ray shuttering mechanism provided in accordance with the invention;

FIG. 2 is a block diagram of apparatus provided in accordance with the invention for the analysis of X-rays produced by a laser produced thermonuclear reaction;

FIGS. 3 and 3A are schematic diagrams of solid state X-ray shutters in accordance with embodiments of the invention wherein acoustic waves are produced by piezoelectrically exciting the crystal itself with voltage pulses and with microwaves;

FIG. 6 is a schematic diagram illustrating an X-ray shuttering mechanism which makes use of an optical beam, in accordance with another embodiment of the invention;

FIG. 7 is a block diagram illustrating apparatus in accordance with the invention for controlling and measuring X-rays emanating from a laser produced plasma wherein the X-rays are controlled electro-optically; and FIG. 8 is a block diagram schematically illustrating apparatus for measuring the temporal profile of X-rays emitted from a target on which laser pulse energy is incident.

Figure 4:
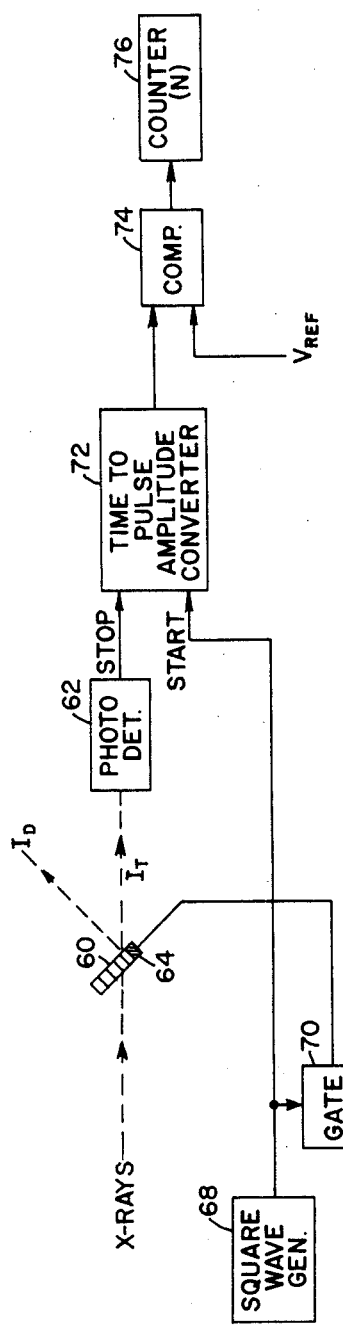
FIG. 4 is a block diagram illustrating apparatus for interrupting anomalous or Bormann transmission through a crystal and measuring such transmission, all in accordance with the invention.

Referring more particularly to FIG. 1, there is shown a crystal 10 suitable for use in X-ray control and analysis apparatus, which apparatus embodies the invention. This crystal may suitably be a rectangular body of silicon. The crystal may be grown from a melt through the use of the Szolchalski process. The crystal is pulled from the melt while rotating the pulling device. This results in a cylindrical body. The body is cut along planes perpendicular to its axis to provide the opposite ends 12 and 14 of the crystal. Cuts are made parallel to the longitudinal axis of the cylindrical body so that the 2, 2, 0 lattice planes are perpendicular to the front face 16 and rear face 18 of the crystal. The crystal is oriented for diffraction in the Lave geometry, so that incoming X-rays $I_I$ arrive at the Bragg angle, $\phi_B$, to the 2, 2, 0 planes. The dimensions of the crystal are selected such that the bending of the lattice planes is small. Suitable dimensions are 5 centimeters in length, 1.2 centimeters in width and 2 millimeters in thickness. The thickness dimension is shown in FIG. 1 as being the dimension between the front and rear faces 16 and 18. The length dimension is the dimension between the ends 12 and 14.

Due to multiple reflections from the planes, energy from a single ray will spread in a direction perpendicular to the planes as this X-ray energy travels through the crystal between the faces 16 and 18. In other words, the energy spread is in a direction between the ends 12 and 14 of the crystal. The dimension of the energy spread is indicated in FIG. 1 as $\lambda_x$. As shown in the drawing, the X-rays pass through the crystal and are transmitted and diffracted; the transmitted rays being indicated as $I_T$ and the diffracted rays as $I_D$. Transmission and diffraction takes place through the crystal in accordance with the Bormann effect and is also known as anomalous transmission. The mechanism of such transmission is described in the above referenced publications, particularly the article by Professor P. P. Ewald. In accordance with the invention, a periodic strain field is introduced into the crystal and has a displacement in a direction perpendicular to the lattice planes (i.e., in a direction between the ends 12 and 14 of the crystal). This periodic strain field is illustrated as a sine wave 20. In accordance with the invention the periodicity or wave length, $\lambda_a$, is comparable to or less than the distance $\lambda_x$ of the energy spread of the X-rays.

This periodic strain field is an acoustic field, which is meant that vibrations are established in the crystal having the desired periodicity or wavelength. The use of the term acoustic should not be taken as restricting such vibrations to audible frequencies. A suitable acoustic frequency, for example, is 10 MHz which affords a wavelength of about 0.8 mm (viz., $\lambda_a$ = 0.8 mm). This wavelength is obtained considering the velocity of propagation of acoustic energy in the crystal to be $10^6$ cm/sec. Inasmuch as the energy spread of the X-ray radiation is greater than the wavelength of the acoustic strain field, the lattice planes in the crystal are displaced such that Bragg's law is no longer satisfied when the acoustic strain field is present. Theoretically, it is believed that the lattice planes are displaced such that they do not remain at the nodes of a standing X-ray wave pattern. Absorption of the X-ray energy can then take place in the atoms of the crystal which are located at the lattice planes.

By exciting the acoustic strain field in the crystal, there is provided a shuttering mechanism for controlling X-ray radiation. By means of the crystal, the X-ray radiation may be controlled quickly, such that fast X-ray excitation processes may be analyzed through the measurement of X-rays which are transmitted through the crystal, either before or after the acoustic strain field is applied. Means provided by the invention for establishing and applying the acoustic strain field and for the measurement and analysis of the X-ray radiation transmitted through the crystal are discussed hereinafter.

Referring now to FIG. 2, there is shown a system for measuring and analyzing X-ray emission from a laser produced plasma which results from a thermonuclear or laser fusion reaction. A high power pulse laser 22 produces a high energy laser pulse which is incident upon a target of moderate atomic number material, such as deuterium or tritium, in a target chamber 24. For further information respecting high energy pulse lasers and appparatus for providing a laser fusion reaction, reference may be had to U.S. Pat. No. 3,723,246 issued to Dr. M. J. Lubin on Mar. 27, 1973. X-rays emanating from the laser produced plasma are incident upon a crystal 26 which is oriented for Bormann or anomalous transmission. Such transmission is indicated as $I_T$ emanating from the rear face of the crystal 26. The crystal 26 may be of the same type as described in connection with FIG. 1. Acoustic waves are launched by means of a transducer 28 and propagate through the crystal in a displacement direction perpendicular to the lattice planes. This transducer is a body of piezoelectric material, such as PZT, which is bonded to an end of the crystal (either the upper end 12 or the lower end 14, as illustrated in FIG. 1).

An oscillator 30 affords a source of high frequency sinusoidal signals. Thus the transducer 28 is excited with the continuous wave A.C. signals. The oscillator 30 is connected to a gate 32 which is normally enabled. The output of the gate 32 is amplified in an amplifier 34 and drives the transducer 28. A continuous wave acoustic signal having a frequency of 10 MHz is therefore launched and exists in the crystal. Bormann or anomalous transmission through the crystal is therefore normally cut off.

When the laser pulse is generated, a portion of that pulse is diverted by means of a dichroic mirror 36 to a photo detector 38. The photo detector triggers a square wave generator 40, such as a one-shot. The output pulse from the square wave generator 40 inhibits the gate 32 and cuts off the continuous wave excitation of the crystal 26 for the period of the pulse from the square wave generator 40. As shown by the waveform adjacent to the output line from the amplifier 34, the driving signal applied to the transducer is a continuous wave, say of 10 MHz, interrupted during the period of the pulse from the square wave generator 40. This period is initiated by the laser pulse (viz., in synchronism therewith) and permits Bormann or anomalous transmission through the crystal 26 for the duration of this pulse.

The X-rays due to the anomalous transmission through the crystal, are applied to an X-ray detector 42 which may consist of a scintillating crystal and a photo multiplier. The signals from the X-ray detector 42 are amplified in an amplifier 44 and are applied to deflect the beam in a Cathode Ray Oscilloscope (CRO) 46. The time base on the oscilloscope is initiated by the leading edge of the square wave pulse from the square wave generator 40. Since the amount of deflection is a function of the intensity of the X-ray radiation anomalously transmitted through the crystal, the display on the oscilloscope is a temporal profile of the X-ray pulse envelope.

Referring to FIGS. 3 and 3A, there are illustrated other crystals 48 similar to the crystal 10 described in connection with FIG. 1 and the crystal 26 described in connection with FIG. 2, except that the crystal 48 is of piezoelectric material, suitably quartz. A periodic wave may be launched in the crystals 48 by exciting the crystal with a high voltage pulse of short duration as shown in FIG. 3 or with microwave pulses as shown in FIG. 3A. The pulse may be intermittent or repetitive, as when repetitive shuttering action is desired. In FIG. 3, excitation of the crystal is implemented by a pulse generator 50 which produces pulses either when triggered or repetitively at a certain rate, say 1000 pulses/sec. These pulses enable a voltage amplifier 52 which may be a tube-type amplifier of the type used in television cathode-ray tube deflection circuits and which generates a high voltage pulse. This high voltage pulse is applied between electrodes 54 and 56 bonded to opposite ends of the crystal 48 (viz., ends which are parallel to the lattice planes in the crystal). In FIG. 3A the pulse is obtained from a microwave pulse generator 49, e.g., a pulsed magnetron and coupled to an end face of the crystal by a wave guide 51 and matching horn 53. An acoustic wave is launched due to the contraction and expansion of the crystal at the leading edge and trailing edge of the high voltage pulse or by the microwave pulse. This acoustic wave operates to disrupt Bormann or anomalous transmission through the crystals 48.

Referring to FIG. 4, there is shown apparatus for measuring anomalous transmission of X-rays through a crystal 60 during the intervals that such transmission is switched off by means of an acoustic strain wave which propagates through the crystal. The crystal is oriented for Laue diffraction such that anomalous transmission of X-rays, $I_T$, through the crystal is incident on a photo detector 62. The photo detector 62 may be similar to the detector 42 described in connection with FIG. 2. The acoustic waves are launched in the crystal 60 by a piezoelectric transducer 64 mounted on one end thereof A high frequency oscillator 66 generates a continuous wave, suitably at 10 MHz. A square wave generator 68 produces a repetitive pulse train having a repetition rate, say of 1 KHz. A gate 70 is enabled by the pulses from the square wave generator 68, such that a repetitive train of bursts of high frequency signals each of duration $T_0$ to $T_1$ is applied to the transducer 64. Anomalous transmission to the crystal is terminated or at least substantially reduced for the duration of each burst.

The leading edge of each pulse from the square wave generator triggers the start input of a time-to-pulse amplitude converter. The output of the photo detector 62, when it reaches a certain level of voltage which corresponds to a certain X-ray intensity, is applied to the stop input of the converter 72. The photo detector output level which provides a stop trigger to the converter 72, may be suitably a level equal to twice the level of the photo detector output under conditions when the acoustic wave is established in the crystal 60. The time-to-pulse amplitude converter 72 may be a commercial instrument which provides an output pulse of amplitude corresponding to the interval between the start and stop trigger pulses which are applied thereto. A suitable instrument may be procured from Ortec, Inc., of Oak Ridge, Tennessee, their Model 457. The output of the converter 72 is applied to one input of a comparator 74. A reference voltage, which may be adjustable, is applied to the other input of the comparator. When the amplitude of the converter output pulse equals the reference voltage amplitude, a pulse is produced by the comparator 74 which is counted in a counter 76. The count registered in the counter is a factor related to the probability that an X-ray photon is transmitted through the crystal 60 by the anomalous transmission mechanism during the intervals $T_o$ to $T_1$ when the acoustic strain field is established in the crystal 60, and is therefore a measure of the shuttering efficiency of the crystal 60.

Consider that the acoustic wave requires a finite time to propagate through the crystal, for example, an acoustic wave propagating at a velocity of $10^6$cm/sec requires about 50 nano seconds to cut off anomalous transmission to the crystal. During the period from $T_o$ until a time thereafter when anomalous transmission is cut off, the X-ray shutter provided by the crystal is open. Thereafter the shutter is closed. The propagation time may be reduced or substantially eliminated by the use of optical means for stimulating the acoustic wave, as will be described hereinafter in connection with FIGS. 6 to 8.

Figure 5:
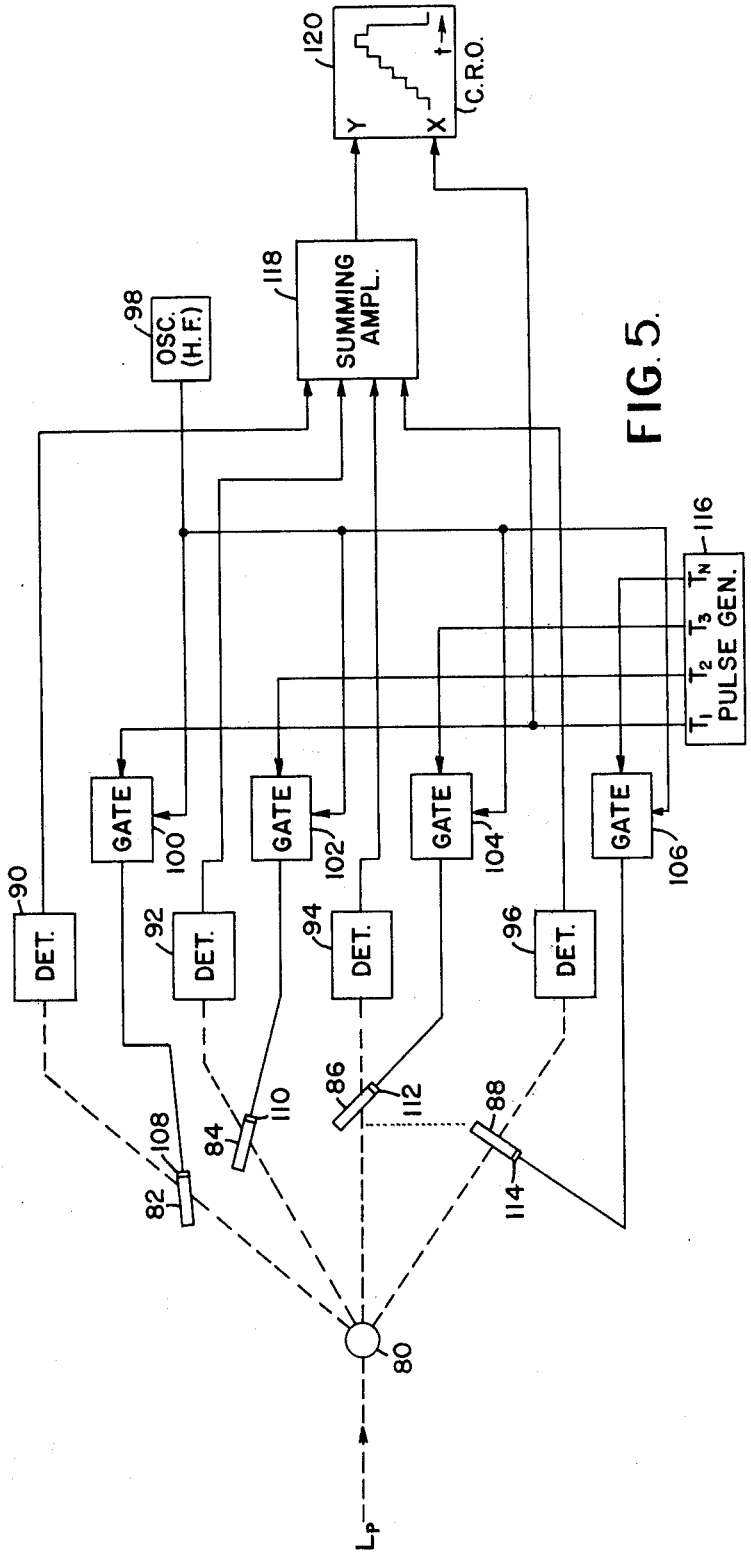
FIG. 5 is a block diagram illustrating apparatus for measuring the temporal profile of X-ray transmitted from a target.

A temporal profile of the X-ray radiation, as when a laser pulse $L_p$ strikes a target 80 may be obtained by the apparatus shown in FIG. 5. A plurality of crystals 82, 84, 86 and 88 are disposed about the target, each for transmitting X-rays emanating from the target in a different direction. While four crystals 82 to 88 are shown, a larger number as indicated by the dash lines in FIG. 5, may be provided to obtain a higher resolution in measurements of the X-ray transmission characteristics. Each of the crystals 82 to 88 is oriented for Laue diffraction of X-rays in a different direction. The X-rays which are anomalously transmitted by each crystal are detected by separate detectors 90, 92, 94 and 96, which may be scintillating crystal photo multiplier detectors of the type described above in connection with FIG. 2. A source of high frequency, say 10 MHz oscillations, such as an oscillator 98, is connected through separate gates 100, 102, 104 and 106 to drive separate transducers 108, 110, 112 and 114 on one end of the crystals 82 to 88. The gates 100 to 106 are enabled by pulses produced by a timing pulse generator 116. The leading edge of these pulses occur after successive periods of time. The leading edge of the first pulse occurs at time $T_1$, the second at time $T_2$, the third at time $T_3$ and the last at time $T_n$. The pulses are overlapping such that even the first occurring pulse $T_1$ does not terminate until after the termination of the last pulse $T_n$. The last pulse $T_n$ terminates at the end of the measurement interval. The first pulse $T_1$ is applied to the gate 100 so that an acoustic wave is launched first in the crystal 82. The next occurring pulse $T_2$ enables the gate 102 so that the high frequency driving signal is next applied to transducer 110 of the second crystal 84. Each of the crystals successively receives the high frequency driving signals at its transducer and the anomalous transmissions of X-rays through the crystals are successively cut off.

The outputs of the photo detectors 90 to 96 are applied to a summing junction of a summing amplifier 118. This summing amplifier also integrates the signals applied thereto. For example, it may be an operational amplifier having a capacitor connected in feedback relationship therewith. The integrated output is applied to the Y deflection input of a cathode ray oscilloscope 120. The time base of the oscilloscope 120 is triggered at $T_1$ by the leading edge of the first pulse from the pulse generator 116. The crystals 82 to 88 are each open for anomalous transmission for short, successive periods of time. Each crystal transmits the X-ray radiation from the target 80 during each such successive intervals of time. Since the X-ray radiation is sampled successively by each of the crystals, the total radiation which is measured and displayed on the oscilloscope 120 is a temporal profile of the X-ray intensity variations of the X-rays produced when the laser pulse $L_p$ strikes the target 80.

A faster shuttering action may be obtained through the use of the radiation pressure to directly excite acoustic fields locally in a crystal in a region where the X-rays are incident. Such radiation pressure may be produced by an intense electromagnetic beam, such as a light beam produced by a laser which is incident on the crystal in the region where the X-rays are incident. FIG. 6 illustrates an embodiment where the light beam is incident on an edge 101 of a crystal 103 so as to excite an acoustic field 105 in a region transverse to X-rays which are incident on a front face of the crystal. FIGS. 7 and 8 illustrate embodiments where the light beam and X-rays are both incident in the same area of the front face of a crystal. The crystals are oriented for anomalous transmission of X-rays which are incident upon the face of the crystal in the same region as the light beam. It is believed, without inferring or implying any limitation to any particular theory, that acoustic fields of fast rise time, since they are not dependent upon acoustic propagation, occurs due to a stimulated Brillouin effect, by means of which the optical beam creates an acoustic wave in the crystal by locally generated electrostriction. Such acoustic fields may build up very rapidly and be of extremely small wavelength, such acoustic frequencies may be greater than 10 GHz.

The apparatus shown in FIG. 6 is operative in the streak mode. A laser 107 produces an optical pulse having a fast rise time and relatively long duration, suitably several microseconds, as by holding the flashlamps on for that period of time. A strip of X-ray sensitive film 109 or an array of X-ray detectors detects the anomalous transmission $I_T$ through the crystal as it is cut off by the optical pulse. The pattern or the film 109 is a streak in the direction between the edges of the crystal which follows the progressive cut-off of anomalous transmission during the optical pulse period.

Alternatively the crystal 103 may be oriented with respect to the incident X-rays, $I_I$, at an angle which differs slightly from the Bragg angle. When the optical pulse, which is preferably a short pulse, say less than one microsecond duration, but having fast use time, is incident upon the crystal edge 101, an aperture for anomalous transmission through the crystal is opened which moves in the direction between the edges of the crystal thereby exposing a streak on the film 109.

FIG. 7 illustrates X-ray control and analysis apparatus which uses a laser beam to launch an acoustic wave in a crystal 130 which is oriented in the path of X-rays from a laser target in a chamber 132 so as to interrupt the anomalous transmission of these X-rays. A photo detector 134 opposite the rear face of the crystal 130 detects and measures the intensity of the anomalously transmitted X-rays. The output of the photo detector is amplified in an amplifier 36 and applied to the Y deflection input of a cathode ray oscilloscope 138.

A timing generator 140 uses two successive timing pulses at successive times $T_1$ and $T_2$. These pulses enable switches 142 and 146 which apply a voltage to the pumping means 148 and 150 of a main laser 152 and a control laser 154. These pumping means may consist of flash lamps which receive voltages from capacitor banks (the voltages being indicated at +V) so as to flash the lamps.

Upon occurrence of the first flash at time $T_1$, the main laser 152 is pumped and a laser pulse, focused by a lens 156, hits a laser fuel material in target chamber 132. X-rays are then produced. Shortly thereafter at time $T_2$, the switch 146 is operated and laser 154 is pumped so as to provide an optical beam. This beam is focused by a lens 158 on the front face of the crystal 130 in the location where the X-rays from the target 132 are incident. Acoustic waves are then launched in the crystal as by means of the stimulated Brillouin effect mentioned above. The anomalous transmission of X-rays through the crystal is cut off with extreme rapidity. During the period between $T_1$ and $T_2$, the X-rays which are anomalously transmitted are displayed on the oscilloscope 138. The time base of the oscilloscope commences at the time $T_1$ since it is triggered by the first timing pulse at time $T_1$. Accordingly, a temporal display of the X-ray emission characteristics, resulting from the laser plasma produced at the target by the pulse from the main laser 152, is displayed and may be measured.

Referring to FIG. 8, a laser 160 provides a pulse of high intensity optical energy which is focused and made incident on a target 162 by a lens 164 so as to produce a laser atomic particle emission reaction which generates X-rays. These X-rays emanate from the target in different directions. A plurality of crystals, only three crystals 166, 168 and 170 being shown to simplify the illustration, are disposed along different ray paths and oriented for anomalous X-ray transmission to photo detectors 172, 174 and 176. The outputs of these photo detectors 172, 174 and 176 are applied to an integrating summing amplifier 178 which operates a cathode ray oscilloscope display 180 in the same manner as the summing amplifier 178 and the cathode ray oscilloscope 120 described in connection with FIG. 5.

Anomalous transmission through the crystals 166, 168 and 170 is interrupted by beams from an auxiliary laser 182 which is pumped by optical energy from the main laser 160. Such energy is diverted to the laser 182 by means of a dichroic mirror 184. Accordingly, immediately after the laser 160 produces its pulse, the laser 182 is pumped. An optical pulse produced by the laser 182 is split into a plurality of beams which are incident on the front face of the crystals 166, 168 and 170 by a lens 184 and echelon 186 arrangement. The lens 184 and echelon 186 are disposed to provide ray paths of successively longer length to successive ones of the crystals 166, 168 and 170. The ray paths to the crystal 170 is shortest. The path to the crystal 168 is longer and the path to the crystal 166 is longest. The beams from the auxiliary laser 182 serve to launch acoustic waves in the crystals in the vicinity where the X-rays from the target 162 are incident thereon; thus interrupting anomalous transmission through the crystals. Since the ray paths to the crystals 166, 168 and 170 are successively longer, the X-ray transmission will be interrupted at successive periods of time. Accordingly, the X-rays from the target 162 will be successively sampled so that, when these rays are translated into electrical signals by the photo detectors 172, 174 and 176, and summed and integrated in the amplifier 178, a display corresponding to the temporal profile of the X-ray pulse envelope generated by the laser fusion reaction of the target 162 will be generated on the oscilloscope 180.

The oscilloscope 180 is synchronized by the beam to the earliest operating one of the crystals 170 by means of a photo detector 190 which receives a portion of the laser beam which is incident on the crystal 170. The crystal 170 is the first of the crystals in which anomalous transmission is interrupted. Immediately prior to the interruption of X-ray transmission through the crystal 170, the photo detector 190 generates a signal. This signal triggers a pulse generator 192, which may be a one-shot, the output pulse from the one-shot is applied to trigger the time base (or X axis sweep) of the oscilloscope display.

From the foregoing description it will be apparent that there has been provided improved methods of and apparatus for controlling, analyzing and measuring X-ray radiation, and particularly X-ray radiation which results from fast X-ray excitation processes such as can occur in a laser produced plasma as may result from a laser fusion reaction. While various embodiments of the methods and apparatus provided by the invention have been disclosed, it will be appreciated that variations and modifications thereof within the scope of the invention will undoubtedly suggest themselves to those skilled in the art. Accordingly, the foregoing description should be taken merely as illustrative and not in any limiting sense.

What is claimed is:
1. The method of analysis of X-ray radiation which comprises the steps of
   orienting a crystal in the path of said radiation to enable anomalous transmission therethrough in accordance with the Bormann effect,
   introducing temporarily different conditions of strain in a direction transverse to the lattice planes of said crystal whereby to enable and inhibit the anomalous transmission through said crystal, and
   measuring the X-ray radiation transmitted through said crystal.
2. The invention as set forth in claim 1 wherein said step of introducing different conditions of strain is carried out by transmitting acoustic waves through said crystal in said direction.
3. The invention as set forth in claim 2 wherein the wavelength of said acoustic waves does not exceed the distance in said direction over which X-rays from a point source incident on one face of said crystal spread as said X-rays pass through said crystal to the face thereof opposite to said one face.
4. The invention as set forth in claim 1 wherein said step of introducing said different conditions of strain is carried out by temporarily applying strain to said crystal in said direction for a certain period of time which is short relative to the period when said strain is removed.
5. The invention as set forth in claim 1 wherein said step of introducing said different conditions of strain is carried out by continuously applying strain in said direction, and removing said strain for a period of time which is short relative to the period when said strain is applied.
6. The invention as set forth in claim 3 wherein said step of transmitting acoustic waves is carried out by periodically applying bursts of acoustic waves to said crystal.

7. The invention as set forth in claim 3 wherein said step of transmitting acoustic waves is carried out by continuously applying acoustic waves to said crystal, and periodically cutting off the application of said acoustic waves.

8. The invention as set forth in claim 3 wherein said step of applying acoustic waves is carried out by piezoelectrically exciting said crystal with electrical signals.

9. The invention as set forth in claim 8 wherein said electric signals have a frequency in a range much higher than the upper end of the acoustic frequency range.

10. The invention as set forth in claim 3 wherein said crystal is of piezoelectric material and said step of applying acoustic waves is carried out by applying and removing a high voltage electric field extending between opposite ends of said crystal, which ends are substantially coplanar with said lattice planes.

11. The invention as set forth in claim 3 wherein said crystal is of piezoelectric material and said step of applying acoustic waves is carried out by applying bursts of microwave energy upon an end of said crystal which is substantially coplanar with said lattice planes.

12. The invention as set forth in claim 3 wherein said step of applying acoustic waves is carried out by directing a beam of optical energy upon said crystal in a region thereof adjacent where said X-rays are incident.

13. The invention as set forth in claim 12 wherein said optical energy is directed to be incident upon an edge of said crystal at a location which is in approximately the same plane as the X-rays which are incident upon a face of said crystal.

14. The invention as set forth in claim 3 wherein said step of applying acoustic waves is carried out by directing a beam of optical energy to be incident upon a face of said crystal in approximately the same location on said face where said X-rays are incident.

15. The invention as set forth in claim 12 wherein said optical energy beam is in the form of a burst.

16. The invention as set forth in claim 3 wherein the step of transmitting acoustic waves through said crystal in said direction is carried out with the aid of an electrostrictive transducer mounted on an end of said crystal which is substantially perpendicular to said direction, and including the step of applying periodic signals to said transducer.

17. The invention as set forth in claim 16 wherein said step of applying periodic signals includes the step of applying said signals in a burst.

18. The invention as set forth in claim 16 wherein the frequency of said signals is of the order of 10 MHz.

19. The invention as set forth in claim 18 wherein said signals are applied to said transducer in bursts, which bursts occur repetitively.

20. The invention as set forth in claim 1 wherein said X-rays emanate from a target, and wherein said orienting step consists of the step of orienting a plurality of crystals in locations spaced from each other about said target to enable anomalous transmission of X-rays which emanate from said target in a plurality of directions, the X-rays emanating in different directions being incident upon different ones of said plurality of crystals.

said strain introducing step consists of the steps of sequentially introducing a like change in the condition of strain in different ones of said crystals, the changed condition of strain existing for successive periods of time, and said measuring step includes measuring the anomalous X-ray radiation transmitted through each of said crystals.

21. The invention as set forth in claim 20 wherein said strain introducing step is carried out by the step of launching acoustic waves through each of said crystals in a direction perpendicular to the lattice planes thereof.

22. The invention as set forth in claim 21 wherein said acoustic waves are launched by generating a periodic signal having a wavelength in said crystals less than the distance, in a direction perpendicular to the lattice planes thereof, which X-rays spread in passing through said crystal in a direction parallel to said planes, and electrostrictively exciting different ones of said crystals separately with different successively occurring ones of said bursts.

23. The invention as set forth in claim 21 wherein said acoustic waves are launched by generating a plurality of light beams, different ones of which occur at successive intervals of time, and directing different ones of said light beams so that they are incident upon different ones of said crystals in approximately the same location on said crystals as where said X-rays are incident.

24. Apparatus for the control of X-ray radiation which comprises a crystal having lattice planes spaced from each other from one end of said crystal to an opposite end thereof, said crystal being disposed in the path of said X-ray radiation so that said X-rays are incident on one face of said crystal at angle to said lattice planes to enable anomalous transmission through said crystal from said one face to the face thereof opposite to said one face in accordance with the Bormann effect, and means for exciting a strain field in a direction between said ends of said crystal for selectively inhibiting and enabling said anomalous transmission whereby to control said X-ray radiation.

25. The invention as set forth in claim 24 wherein said crystal consists of piezoelectric material and said exciting means comprises means for generating a high voltage electric pulse, and means responsive to said pulse for generating an electric field in a direction between said ends of said crystal for exciting acoustic vibration in said crystal.

26. The invention as set forth in claim 24 wherein said means for exciting said strain field comprises means for launching an acoustic strain field in said crystal having a wavelength in said direction less than the distance in said direction which X-ray radiation spreads as it passes between said faces of said crystal.

27. The invention as set forth in claim 26 wherein said launching means comprises means for exciting said transducer into acoustic vibration at a frequency of at least 10 MHz.

28. The invention as set forth in claim 24 wherein said exciting means comprises an electroacoustic transducer mounted on said one end of said crystal, and means for applying periodic electric signals to said transducer.

29. The invention as set forth in claim 28 wherein said applying means includes means for generating bursts of high frequency electric signals which occur repetitively.

30. The invention as set forth in claim 28 wherein said applying means includes means for generating a continuous wave high frequency signal, and means for inhibiting said signal for a predetermined period of time.

31. The invention as set forth in claim 30 wherein said X-rays are generated when a target is illuminated by a high energy pulse of laser energy, and said applying means includes means for detecting said laser pulse, means for producing a control pulse having duration equal to said predetermined period of time when said laser pulse is detected, and means for applying said control pulse to said inhibiting means.

32. The invention as set forth in claim 24 wherein said exciting means comprises means for generating a pulse of optical energy which is incident on said crystal in about the same region thereof as said X-rays.

33. The invention as set forth in claim 32 wherein said exciting means includes means for generating a beam of said optical energy which is incident upon an edge of said crystal, the location of incidence of said beam and X-rays being in the same plane mutually perpendicular to said edge and said one face.

34. The invention as set forth in claim 32 wherein said optical energy provided by said exciting means is a beam, said beam being incident on said one face in about the same location as said X-rays.

35. The invention as set forth in claim 34 wherein said X-rays are provided by a first laser which produces a pulse of high intensity light which is incident on a target, said first laser having pumping means operative when enabled to provide said high intensity pulse, said exciting means comprising a second laser having pumping means operative when enabled to cause said second laser to produce said pulse of optical energy which is incident on said one face of said crystal, means for successively operating said first laser pumping means, and said second laser pumping means, and means for measuring the anomalous X-ray transmission through said crystal during a period commencing when said first laser pumping means is operated.

36. The invention as set forth in claim 24 wherein a plurality of said crystals are provided each for receiving X-rays emanating in a different direction from a source thereof, said exciting means includes means for exciting different ones of said crystals successively, and means responsive to anomalous X-rays transmission through said crystals for providing an output signal representing the intensity of said X-ray radiation from said source.

37. The invention as set forth in claim 36 wherein said exciting means comprises a plurality of electrostrictive transducers mounted on a different one of said plurality of transducers at said one end thereof, a source of high frequency oscillations, and means for successively connecting said source to different ones of said transducers.

38. The invention as set forth in claim 36 wherein said exciting means comprises a laser which produces a high intensity pulse of light, and means for splitting said laster pulse into a plurality of beams, along paths of different length, each incident upon a different one of said crystals in the same region thereof where said X-rays are incident thereon.

39. The invention as set forth in claim 38 wherein said splitting means includes an echelon disposed in the path of illumination from said laser.

40. The invention as set forth in claim 24 including means for measuring the anomalous X-ray radiation transmitted through said crystal so that the temporal characteristics of said radiation can be analyzed.

41. The invention as set forth in claim 40 wherein said exciting means comprises a piezoelectric transducer mounted on said one end of said crystal, a source of pulses having a certain repetition rate, a high frequency oscillator providing A.C. signals of frequency much higher than said repetition rate, gate means operated by said pulses for applying said A.C. signals to said transducer for the duration of said pulses, and wherein said measuring means includes an X-ray detector disposed in the path of anomalous X-ray transmission through said crystal and providing an output in response to said anomalously transmitted X-rays, means for converting the intervals of time between the onset of each of said pulses and said outputs into output pulses having amplitudes corresponding to the duration of said intervals of time, and means for counting each of said pulses which exceed a certain amplitude.

* * * * *